United States Patent [19]

Tschanz et al.

[11] 4,155,966
[45] May 22, 1979

[54] METHOD OF MAKING A CATHETER

[75] Inventors: August E. Tschanz, Lansdale; Robert W. Geiger, Geigertown, both of Pa.

[73] Assignee: Teleflex Incorporated, Limerick, Pa.

[21] Appl. No.: 872,072

[22] Filed: Jan. 25, 1978

Related U.S. Application Data

[62] Division of Ser. No. 743,038, Nov. 18, 1976, Pat. No. 4,095,598.

[51] Int. Cl.² ............................................. B29C 23/00
[52] U.S. Cl. ..................................... 264/25; 264/230; 264/274; 264/327; 264/345
[58] Field of Search ................. 264/25, 230, 274, 296, 264/322, 327, 80, 345, 5, 9, 521

[56] References Cited
U.S. PATENT DOCUMENTS

| | | | |
|---|---|---|---|
| 2,378,901 | 6/1945 | Amrhein | 264/274 X |
| 3,000,057 | 9/1961 | Swedlow | 264/80 X |
| 3,092,439 | 6/1963 | Harrison | 264/230 X |
| 3,545,168 | 12/1970 | Day | 264/322 X |
| 3,929,943 | 12/1975 | Klimaszewski | 264/322 X |

*Primary Examiner*—Thomas P. Pavelko
*Attorney, Agent, or Firm*—McGlynn and Milton

[57] ABSTRACT

A catheter assembly including a plastic tube having a cup-shaped bulb at one end and which is oval in cross section. The walls of the bulb are thicker than the remainder of the tube and a hub is molded about the bulb both interiorly and exteriorly thereof. The bulb is formed by placing the tube on a mandrel, which extends from a mandrel carrier, and thereafter placing the carrier on a base so that the upper end of the tube and mandrel extend through a slot and into a heating cavity defined by a housing. The upper end of the tube is subjected to radiant heat on opposite sides thereof to heat the circumference of the tube unevenly to form and define the cup-shaped bulb. The upper end of the tube is heated to a temperature close to its melting point.

8 Claims, 5 Drawing Figures

METHOD OF MAKING A CATHETER

This application is a divisional of application Ser. No. 743,038 filed Nov. 18, 1976 now U.S. Pat. No. 4,095,598.

This invention relates to a catheter assembly and to the method and apparatus for making a catheter assembly. Catheters are utilized in the practice of medicine to establish fluid communication with the veins and/or arteries of the human body. Catheters typically include a plastic tube with a plastic hub molded about one end of the tube. The disposition of the hub about one end of the tube has presented problems with the prior art catheters. Various schemes have been utilized for connecting the tube to the hub; however, these prior art schemes have not proved entirely satisfactory. In some instances the pull-off strength is not sufficient, the pull-off strength being the force necessary to pull or separate the tube from the hub. In other words, the connection between the tube and the hub is frequently not strong enough. Another problem is the occurrence of fluid leakage between the end of the tube and the hub at the connection between the tube and the hub. Somewhat ancillary to these problems is the fact that in many prior art assemblies the tube and the hub are allowed to rotate relative to one another.

Included in the various schemes utilized to connect the tube to the hub portion are multi-part systems such as a collar or sleeve inserted within the end of the tube to force the tube outwardly into engagement with the hub, deformation of the end of the tube to provide a mechanical lock with the hub as the hub is molded thereabout, etc. There is, however, no prior art system which is sufficiently effective in overcoming the problems of pull-off strength, leakage and relative rotation between the hub and the tube.

Accordingly, the subject invention provides a catheter assembly which overcomes the problems associated with the prior art in that it includes a plastic tube having an irregular end with the hub disposed about and contiguous with both the interior and exterior of the irregular end, thereby increasing the pull-off strength to the extent that the tube will break before it may be separated from the hub while at the same time preventing leakage between the tube and the hub.

In a more specific sense, the irregular end of the tube is shaped as a bulb which is oval, as viewed in cross section, and has walls thicker than the walls of the tube.

The irregular end of the tube is formed by placing a tube on a vertical mandrel and heating only the end portion of the tube until it increases in diameter to form the bulb. The apparatus utilized for forming the tube includes means for supporting the plastic tube and heating means for radiantly heating the heat zone for heating a predetermined length of the end portion of the plastic tube.

Other advantages of the present invention will be readily appreciated as the same becomes better understood by reference to the following detailed description when considered in connection with the accompanying drawings wherein.

Figure 1:
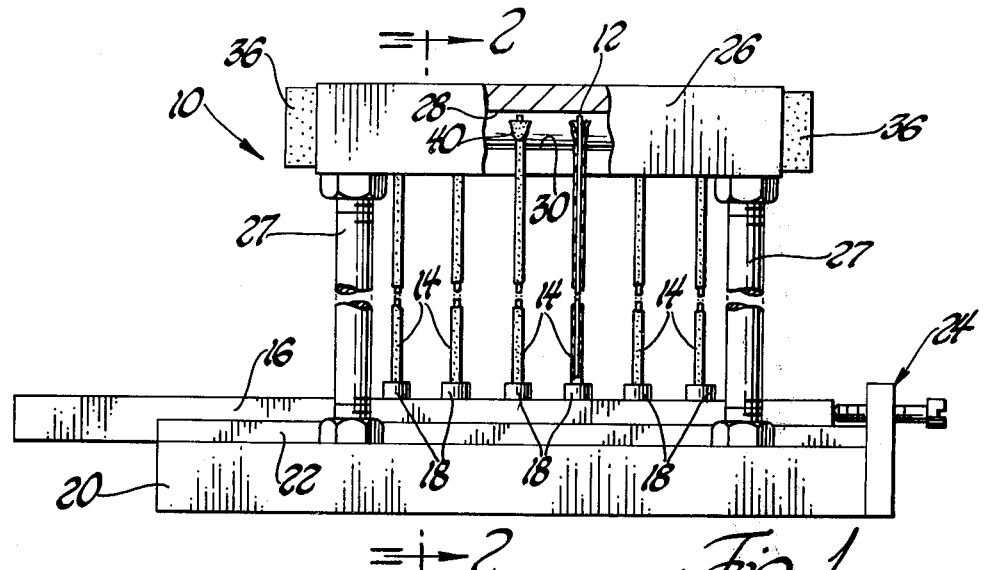
FIG. 1 is a side elevational view partially broken away and in cross section of a preferred apparatus for forming the tube utilized in the catheter assembly of the subject invention.
Figure 2:
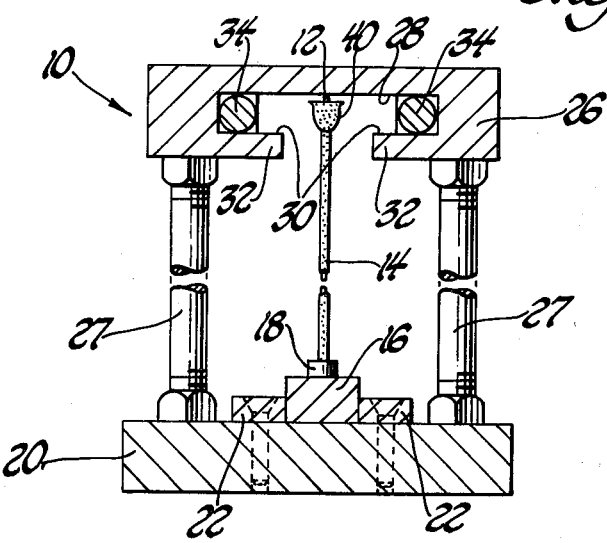
FIG. 2 is a cross-sectional view taken substantially along line 2—2 of FIG. 1.

An apparatus for forming a plastic tube for use in the catheter assembly of the subject invention is generally shown at 10 in FIGS. 1 and 2.

The apparatus 10 includes a means comprising a plurality of vertically disposed mandrels 12 for supporting the plastic tubes 14. The apparatus also includes a mandrel carrier means defined by the carrier bar 16 and individual mandrel supports 18. The mandrel carrier bar 16 is manually movable into and out of the apparatus 10. Specifically, the apparatus 10 includes a base or base means 20 including the positioning blocks 22 and stop means 24 for receiving and positioning the carrier bar 16. The stop means 24 includes a threaded adjusting screw threadedly engaging a bracket to longitudinally align the position of the mandrel carrier means 16.

The apparatus 10 also includes heating means for radiantly heating a heat zone for heating a predetermined length of the end of the plastic tubes 14. More specifically, the heating means includes the housing member 26 which defines a pair of spaced top and bottom walls 28 and 30, respectively. The top and bottom walls 28 and 30 extend generally perpendicular to the mandrels 12. The top wall 28 extends across the top of the mandrels 12 and the bottom wall 30 includes a slot defined by the lips 32 for receiving and through which the upper ends of the mandrels 12 extend. The member 26 is supported upon the base 20 by threaded support posts 27 which have threaded nuts thereon respectively engaging the member 26 and the base 20 for adjusting the vertical position of the member 26 relative to the base 20.

The heating means also includes the heat generating means comprising the heat generating devices defined by the electrical resistance heaters 34. The heaters 34 are disposed between the top and bottom walls 28 and 30 and are spaced inwardly from the edges of the slot defined by the lips 32 whereby the heaters 34 are spaced laterally from the ends of the mandrels 12. The slot defined by the lips 32 is elongated and extends from one end of the member 26 to the other. Insulating members 36 are disposed at each end of the member 26 to close the ends of the slot for retaining the heat generated within the chamber or cavity defined between the top and bottom walls 28 and 30. It will be appreciated that the insulating member 36 on the left end, as viewed in FIG. 1, is removable for inserting and removing the mandrels 12 into and out of the member 26. It will be appreciated that the member 26 defines a generally rectangular chamber or cavity, as viewed in cross section, with the bottom of the rectangle having a slot extending therealong for receiving the ends of the mandrels 12. The extreme or lateral ends of the rectangle shape support the heating devices 34 which provide radiant heat subjected to opposite sides of the tubes disposed on the mandrels 12. The lips 32 also define shields which prevent the heat from being subjected to portions of the tubes other than the extreme end portions, i.e., the predetermined length at the end of each tube which is to be formed into the shape of a cup-shaped bulb.

While the carrier means 16 is removed from the apparatus 10, plastic tubes 14 are disposed upon the mandrels 12. Thereafter the carrier means 16 is disposed on the base member 20 in a position as determined by the guide members 22 and the stop means 24 whereby the predetermined lengths of the upper ends of the tubes 12 are disposed in the heating chamber with the remaining portions of the tubes shielded by the lips 32 from the heat generated in the heating chamber or cavity. The end portion of the tubes are radiantly heated to a temperature which approaches the melting point of the plastic of the tube which, in the preferred embodiment, is a temperature of between 675° F. and 700° F. and for a period of approximately 15 seconds. The plastic tubes 14 remain on the vertically disposed mandrels 12 with their upper ends subjected to the radiant heat until the predetermined length of the end of each tube increases in diameter to form a cup-shaped bulb which has a wall thickness greater than the wall thickness of the remaining portion of the tube Specifically, such cup-shaped bulbs are shown at 40.

Since the heating member 26 is elongated and the heating devices 34 extend therealong on opposite sides of the tubes 14, the opposite sides or portions of the circumference of the tubes 14 are heated differently than the remaining circumference of the tubes. In other words, opposite sides of the tubes 14 are heated differently or at a higher rate and are subjected to a higher temperature than the remainder of the circumference of the upper ends of the tube to define an oval-shaped bulb, as viewed in cross section or as viewed in a direction generally parallel to the axis of each tube 14. Such an oval configuration is shown in FIG. 4.

Figure 3:
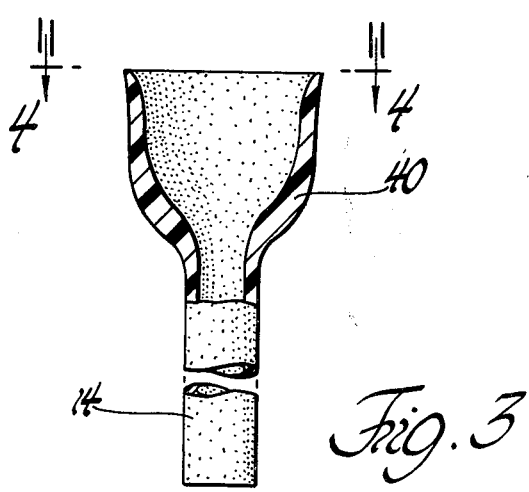
FIG. 3 is a fragmentary cross-sectional view of a tube formed in accordance with the subject invention.
Figure 4:
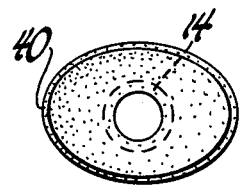
FIG. 4 is a view taken substantially along line 4—4 of FIG. 3.
Figure 5:
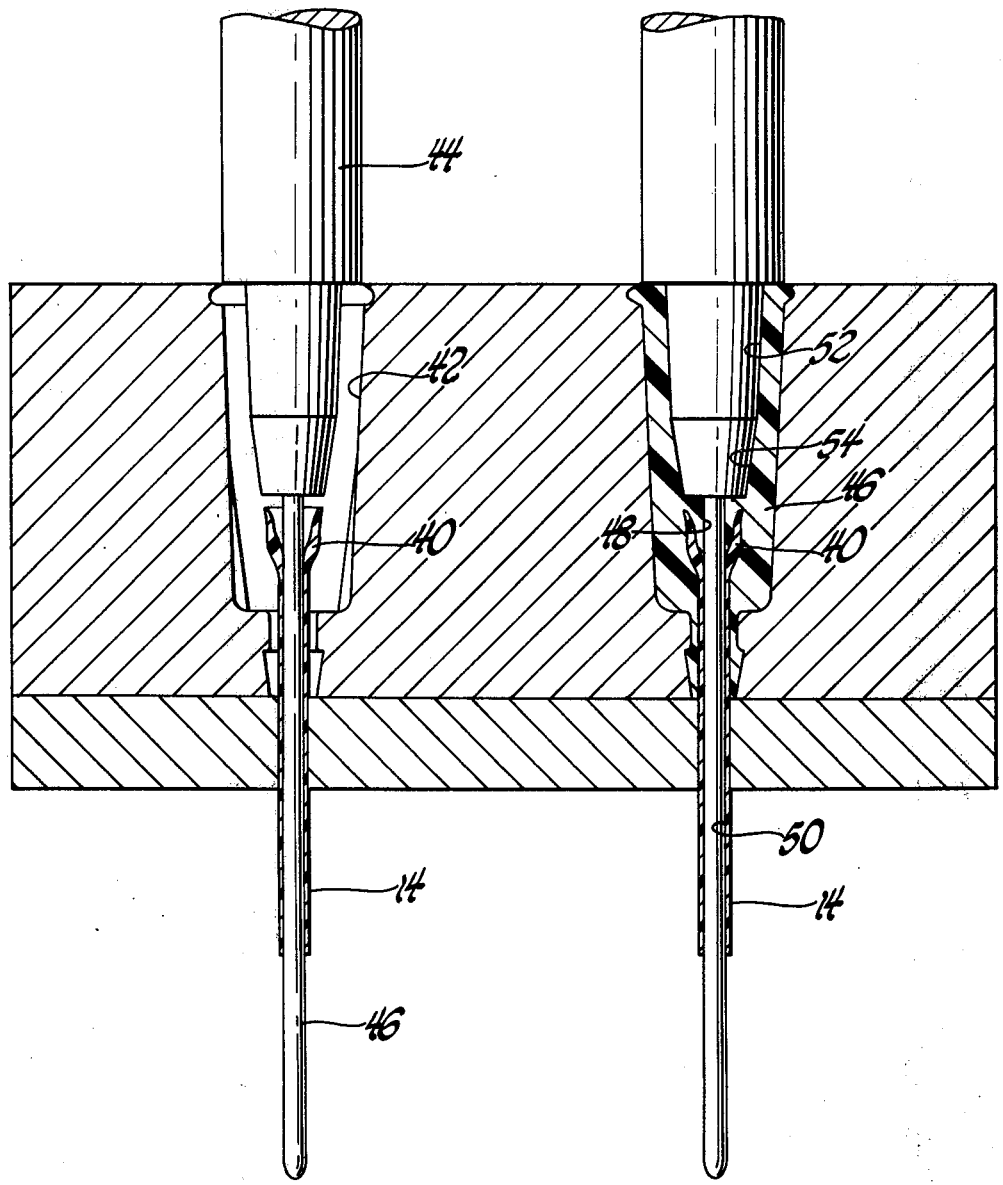
FIG. 5 is an enlarged cross-sectional view showing a mold cavity with the tube disposed therein in a first position and a mold cavity in a second position with the hub portion molded about the end of the tube to define a catheter assembly constructed in accordance with the subject invention.

Once the upper end of a tube is formed into the cup-shaped bulb, as illustrated in FIGS. 3 and 4, it is disposed within a mold cavity 42, as illustrated in the lefthand portion of FIG. 5, with a male mold part 44 disposed within the cavity and including a shaft 46 extending downwardly into the tube 14. Thereafter, a plastic hub is molded about the cup-shaped bulb portion, as illustrated in the righthand portion of FIG. 5. It will be noted that the hub 46, as illustrated in FIG. 5, is molded so that it is disposed or contiguous with both the exterior and the interior of the bulb portion 40. That portion of the hub 46 disposed interiorly of the bulb 40 defines a passage 48 within the bulb 40 which is coaxial and generally of the same diameter so as to be substantially an extension of the inner passageway 50 of the tube 14. The hub 46 includes a cavity 52 which includes a tapered lower portion 54 which communicates with the passage 48.

Thus, as illustrated in FIGS. 3 and 4, the tube 14 includes an irregular end defined by the cup-shaped bulb 40 which is not conformed to the shape of the remainder of the tube 14. The bulb, as viewed in FIG. 4, has an outer periphery which is disposed at different distances radially from the axis of the tube and, more specifically, defines an oval whereby the end portions of the oval are disposed at greater distances from the axis of the tube than are the side portions of the oval. It will be noted that the wall thickness of the bulb 40 is thicker than the remainder of the tube 14. Accordingly, as the wall thickness of the bulb is greater than that of the tube, the pull-off strength or the strength necessary to separate the tube from the hub 46 is greatly increased and to the extent that the tube portion 14 will rip, tear or separate before the bulb portion 40 will be separated from the hub 46. Additionally, as the hub 46 includes a portion disposed interiorly of the bulb 40 there is no leakage between the bulb portion 40 and the hub 46. Further, as the bulb is oval-shaped, relative rotation between the tube 14 and the hub 46 is prevented which further increases the force necessary to separate the two components and prevents the likelihood of leakage between the two components.

Although the subject invention has been described in connection with a catheter, it may be utilized with other plastic tubular members.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

The embodiments of the invention in which an exclusive property or privilege is claimed are defined as follows:

1. In a method of forming a tubular member comprising the steps of; placing a plastic tube on a vertical mandrel, and radiantly heating a predetermined length of the end of the tube from opposite sides thereof to heat opposite portions of the circumference of the tube differently than the remainder of the circumference until the tube increases in diameter and wall thickness along the predetermined length to define a bulb of oval configuration.

2. In a method of making a catheter assembly including the steps of; placing a plastic tube on a vertical mandrel, and heating a predetermined length of the end of the tube from opposite sides thereof to heat opposite portions of the circumference of the tube differently than the remainder of the circumference until it increases in diameter to form a bulb of oval configuration.

3. A method as set forth in claim 2 further defined as heating the predetermined length until the wall thickness thereof increases to form the bulb.

4. A method as set forth in claim 3 further defined as heating the predetermined length at the end of the tube to form a cup-shaped bulb.

5. A method as set forth in claim 4 including molding a plastic hub about the bulb both interiorly and exteriorly thereof.

6. A method as set forth in claim 5 further defined as heating the tube radiantly.

7. A method as set forth in claim 6 further defined as heating the tube at a temperature near the melting point of the plastic tube.

8. A method as set forth in claim 6 further defined as heating the tube at a temperature in the range of 675° F. to 700° F.

* * * * *